(12) United States Patent
Stansbury

(10) Patent No.: US 6,500,156 B1
(45) Date of Patent: Dec. 31, 2002

(54) THUMB-POWERED FLUSHING DEVICE FOR CATHETERS

(75) Inventor: L. Dean Stansbury, Wheat Ridge, CO (US)

(73) Assignee: McKinley Medical L.L.L.P, Wheat Ridge, CO (US)

( * ) Notice: Subject to any disclaimer, the term of this patent is extended or adjusted under 35 U.S.C. 154(b) by 92 days.

(21) Appl. No.: 09/679,194

(22) Filed: Oct. 3, 2000

(51) Int. Cl.[7] ............................................. A61M 11/00
(52) U.S. Cl. ....................... 604/185; 604/132; 604/153; 604/212; 604/257
(58) Field of Search ............................... 604/93.01, 131, 604/132, 151, 153, 181–183, 185, 212, 257, 264, 523, 890.1

(56) References Cited

U.S. PATENT DOCUMENTS

| | | | | |
|---|---|---|---|---|
| 1,988,624 A | * | 1/1935 | Kipp | 604/153 |
| 2,071,127 A | * | 2/1937 | Jones | 604/185 |
| 2,471,623 A | * | 5/1949 | Hubbell | 604/185 |
| 4,291,702 A | | 9/1981 | Cole et al. | |
| 4,341,224 A | | 7/1982 | Stevens | |
| 4,457,487 A | | 7/1984 | Steigerwald | |
| 4,497,468 A | | 2/1985 | Hubbard et al. | |
| 4,624,662 A | | 11/1986 | Le | |
| 5,061,243 A | * | 10/1991 | Winchell et al. | 604/132 |
| 5,267,964 A | * | 12/1993 | Karg | 604/151 |
| 5,389,070 A | * | 2/1995 | Morell | 604/183 |
| 5,588,816 A | * | 12/1996 | Abbott et al. | 604/153 |
| 5,678,557 A | | 10/1997 | Reynolds et al. | |
| 5,738,657 A | | 4/1998 | Bryant et al. | |
| 6,315,762 B1 | * | 11/2001 | Recinella et al. | 604/183 |

* cited by examiner

*Primary Examiner*—J. Casimer Jacyna
(74) *Attorney, Agent, or Firm*—Dorr, Carson, Sloan & Birney, P.C.

(57) ABSTRACT

A catheter flushing device includes a chamber covered with a movable member (e.g., a flexible diaphragm) that can be compressed by exertion of pressure on the diaphragm; and a valve having a first position allowing fluid from a fluid source to fill the chamber, and a second position allowing fluid from the chamber to flow through the catheter when pressure is exerted on the movable member. In particular, the catheter flushing device includes a housing having a cylindrical valve opening, an inlet port for connection with the fluid source, and an outlet port for connection with the catheter. The chamber is defined by a flexible diaphragm sealed about a region of the housing. The chamber can be compressed by manually exerting pressure on the diaphragm by means of a thumb or finger. A passageway extends through the housing from the chamber to the valve opening. A rotatable valve member within the valve opening has a channel directing fluid from the inlet port into the chamber in the first position, and a channel directing fluid from the chamber to the outlet port in the second position. The device can also be equipped with a KVO flow path through the housing between the inlet and outlet ports to maintain a substantially constant, minimal flow from the fluid source to the catheter that bypasses the valve assembly.

12 Claims, 5 Drawing Sheets

*Fig. 10*
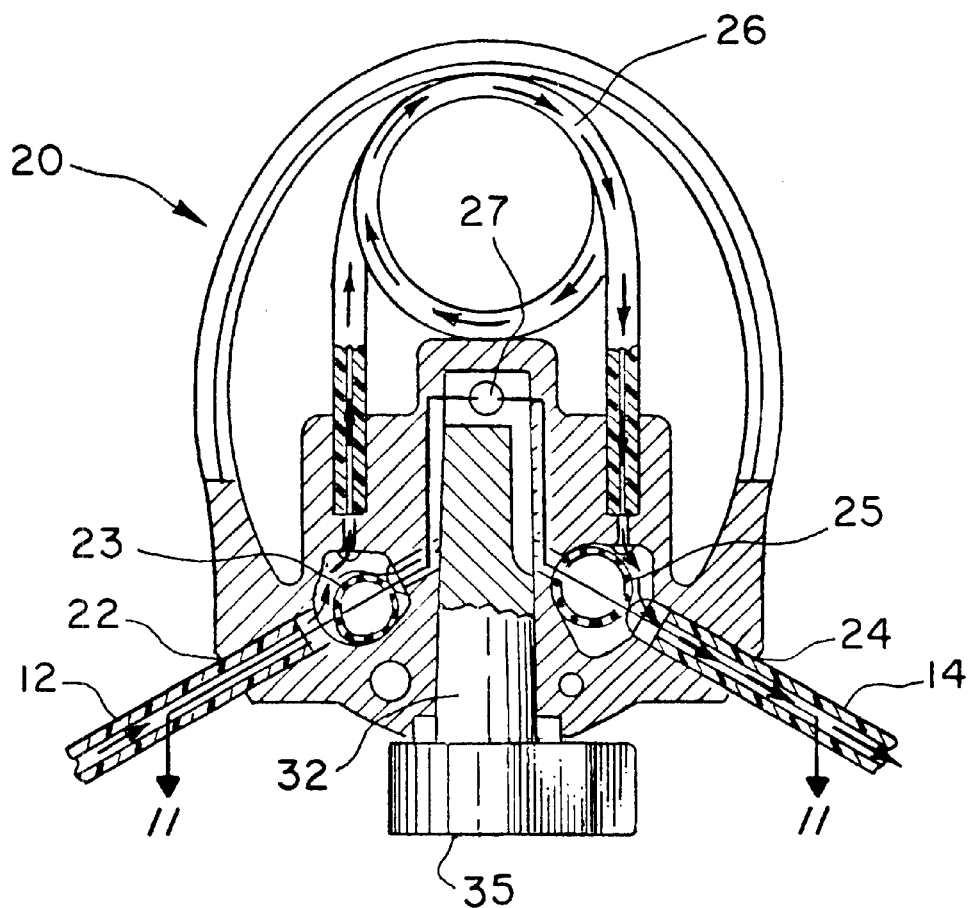
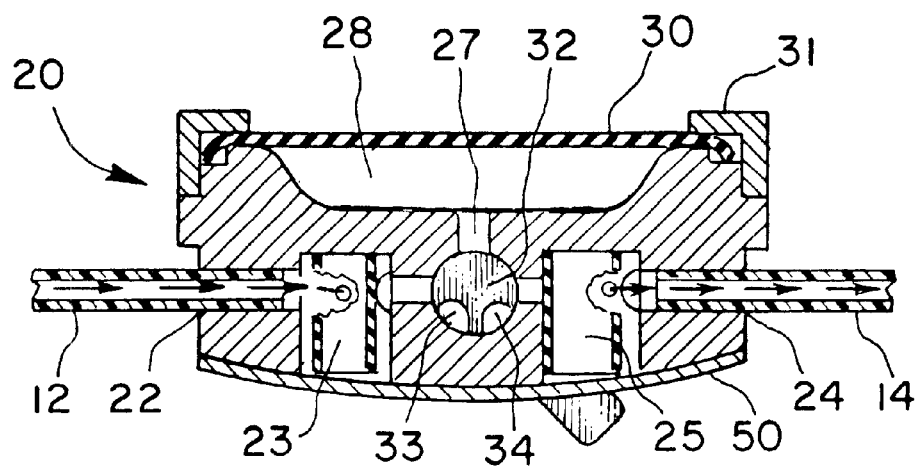
*Fig. 11*

THUMB-POWERED FLUSHING DEVICE FOR CATHETERS

BACKGROUND OF THE INVENTION

1. Field of the Invention

The present invention relates generally to the field of devices for flushing catheters. More specifically, the present invention discloses a thumb-powered flushing device for intravenous catheters.

2. Statement of the Problem

Intravenous catheters have been widely used for many years to administer medications and other fluids to patients. In some instances, medication is administered through the catheter on a continuous basis. However, in other instances, doses of medication are administered on a periodic basis. Patients undergoing long-term drug therapies (i.e., a few to several weeks) will typically have a catheter or "port" surgically installed to facilitate multiple infusions or injections. One of the biological reactions of the body to an implanted catheter is a growth of dendrites or filaments into the end of the catheter. Thus, an important aspect of this process is maintaining an open, free-flowing catheter.

When administering periodic doses of medication, one conventional approach has been to maintain a low-volume, constant flow of saline solution or other fluid (typically in the range of approximately 0.1 to 5.0 ml/hr) through the catheter between doses of medication. This small continual flow, also known as the KVO (keep vein open) flow, helps to keep the catheter and the patient's vein open. The KVO infusion can be provided by an electronic pump, disposable infuser, or an IV drip. The IV line attached to the KVO device typically terminates in an injection site (e.g., a Y-site as illustrated in FIG. 1) at the patient. In the case of a conventional Y-site, one branch of the Y-site has a rubber seal that permits medication or other fluids to be injected from a syringe through the rubber seal and into the catheter, without the need to disconnect the KVO flow.

The KVO flow is sometimes insufficient to maintain patency of the catheter. Therefore, many healthcare professionals inject a quantity of saline solution (about 3 ml) via syringe through the rubber seal of the Y-site to ensure patency of the catheter prior to administering each dose of medication. Several of these flushes may be required each day, usually just prior to injections of medication. This approach is effective, but adds time and expense to the procedure.

The prior art in the field also includes the following flushing devices for catheters:

| Inventor | Patent No. | Issue Date |
| --- | --- | --- |
| Cole et al. | 4,291,702 | Sep. 29, 1981 |
| Stevens | 4,341,224 | July 27, 1982 |
| Steigerwald | 4,457,487 | July 3, 1984 |
| Hubbard et al. | 4,497,468 | Feb. 5, 1985 |
| Le | 4,624,662 | Nov. 25, 1986 |
| Reynolds et al. | 5,678,557 | Oct. 21, 1997 |
| Bryant et al. | 5,738,657 | Apr. 14, 1998 |

Cole et al. disclose a catheter flushing device with a valve plunger having a capillary passage that provides a first low-flow path. When the plunger is moved from its seat, a second high-flow path is established that flushes the apparatus. Stevens discloses a similar device.

Reynolds et al. disclose a flush device for an intravenous blood pressure monitoring system that includes a continuous flow channel and a fast flush channel. In particular, the flush device has a generally tubular housing containing a plunger surrounded by an elastomeric member. When the plunger is in its raised position, the elastomeric member is relaxed and restricts flow through the housing to a small capillary channel. When the plunger is depressed, the elastomeric member stretches and creates a larger channel for fluid flow between the elastomeric member and the interior surface of the housing, which permits a fast flush flow through the device.

Steigerwald, Hubbard et al., and Le disclose other examples of catheter flushing devices with push-button valve mechanisms that provide both slow flow and fast flush modes.

Bryant et al. disclose an ambulatory infusion system having a gas-pressurized bladder to discharge solution from an adjacent bag. Internal gas pressure is developed within the bladder by a chemical reaction. The tubing set leading from the solution bag includes a flow restrictor that can be sized to provide minimal flow rates.

3. Solution to the Problem

None of the prior art references uncovered in the search show a catheter flushing device using a thumb-powered movable member (e.g., a flexible diaphragm) to propel fluid through the catheter, and a valve that regulates flow into and out of the chamber beneath the movable member. This configuration has significant safety advantages in that it prevents accidental backflow or uncontrolled forward flow through the device to the patient. The present device can be used to deliver a small quantity of fluid to flush a catheter, or alternatively can be used to deliver a bolus of medication. The present device can also be used to provide a continuous low-volume flow (i.e., a KVO flow) to the catheter between doses.

SUMMARY OF THE INVENTION

This invention provides a catheter flushing device that includes a chamber covered with a movable member (e.g., a flexible diaphragm) that can be compressed by exertion of pressure on the movable member; and a valve having a first position allowing fluid from a fluid source to fill the chamber, and a second position allowing fluid from the chamber to flow through the catheter when pressure is exerted on the movable member. In particular, the catheter flushing device includes a housing having a cylindrical valve opening, an inlet port for connection with the fluid source, and an outlet port for connection with the catheter. The chamber is defined by a movable member sealed to a region of the housing. The chamber can be compressed by manually exerting pressure on the movable member by means of a thumb or finger. A passageway extends through the housing from the chamber to the valve opening. A rotatable valve member within the valve opening has a channel directing fluid from the inlet port into the chamber in the first position, and a channel directing fluid from the chamber to the outlet port in the second position. The device can also be equipped with a KVO flow path through the housing between the inlet and outlet ports to maintain a substantially constant, minimal flow from the fluid source to the catheter that bypasses the valve assembly.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 10 is a horizontal cross-sectional view of the device with the valve in an intermediate position allowing only KVO flow.

FIG. 11 is a vertical cross-sectional view of the device corresponding to FIG. 10.

DETAILED DESCRIPTION OF THE INVENTION

Figure 1:
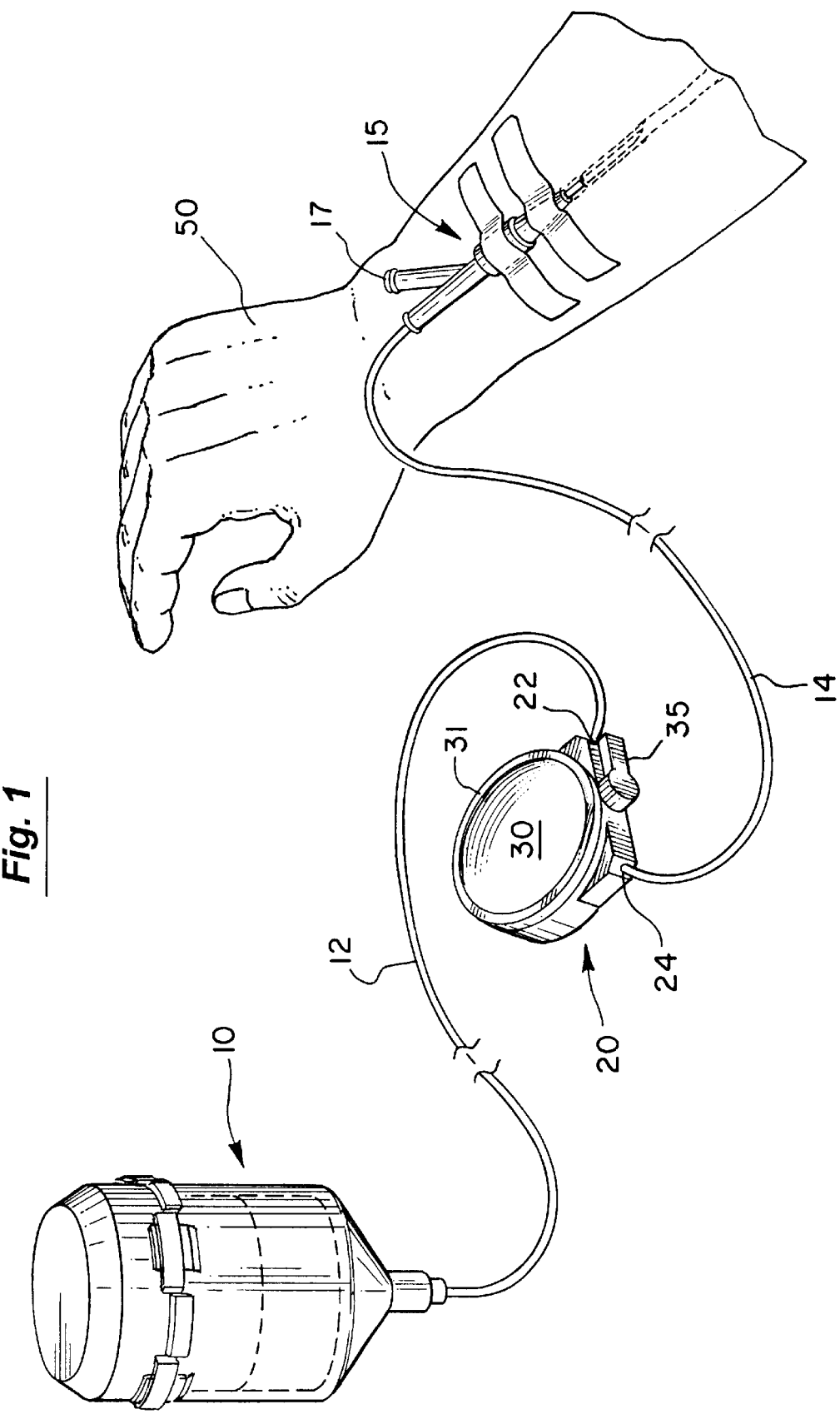
FIG. 1 is a perspective view of the present device 20 connected in the tubing between an infusion pump 10 and a catheter 15.

Turning to FIG. 1, a perspective view is provided showing the present device 20 connected in the tubing between an infusion pump 10 and a catheter 15. Any type of infusion pump can be employed as a source of fluid to be administered to the patient 50 via the catheter 15. Alternatively, fluid can be supplied by gravity from an elevated IV bag. Conventional fluid sources deliver fluid at a pressure of approximately 6 psi, although the present device will work satisfactory at pressures ranging down to approximately 1 to 1.5 psi.

Similarly, any type of catheter 15 can be used. The drawings illustrate a conventional intravenous catheter 15 inserted into a vein in the hand of a patient 50. The proximal portion of the catheter 15 includes a injection site 17. For example, the injection site 17 can be a Y-site having a first branch that can be connected to the fluid source 10, and a second branch with a resilient cap that can be used for injection of medication from a syringe. For the purposes of this invention, it should be expressly understood that "catheter" should be interpreted to include any type of device having a lumen for delivering medication or other fluids to any part of a patient, or for draining fluid from a patient. This includes, but is not limited to intravenous catheters, injection sites, vascular access devices, transtracheal catheters, endotracheal tubes, and catheters used for delivery of anesthetics.

Figure 2:
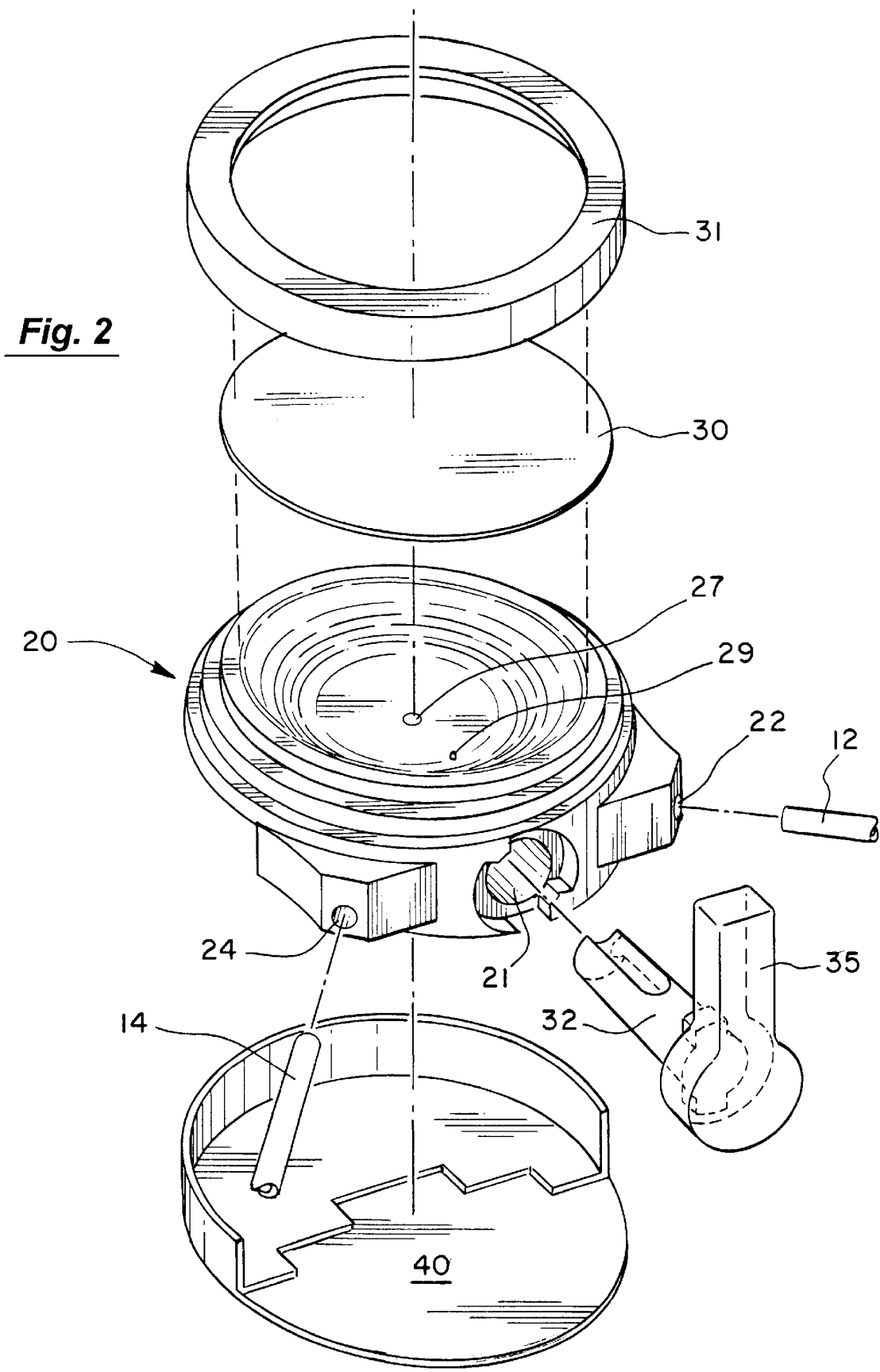
FIG. 2 is an exploded perspective view of the present device 20.
Figure 3:
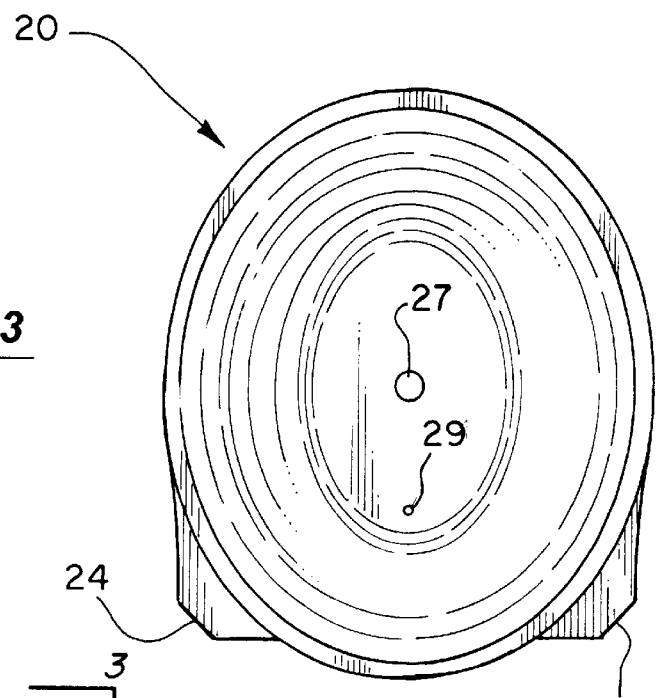
FIG. 3 is a top view of the housing of the device.
Figure 4:
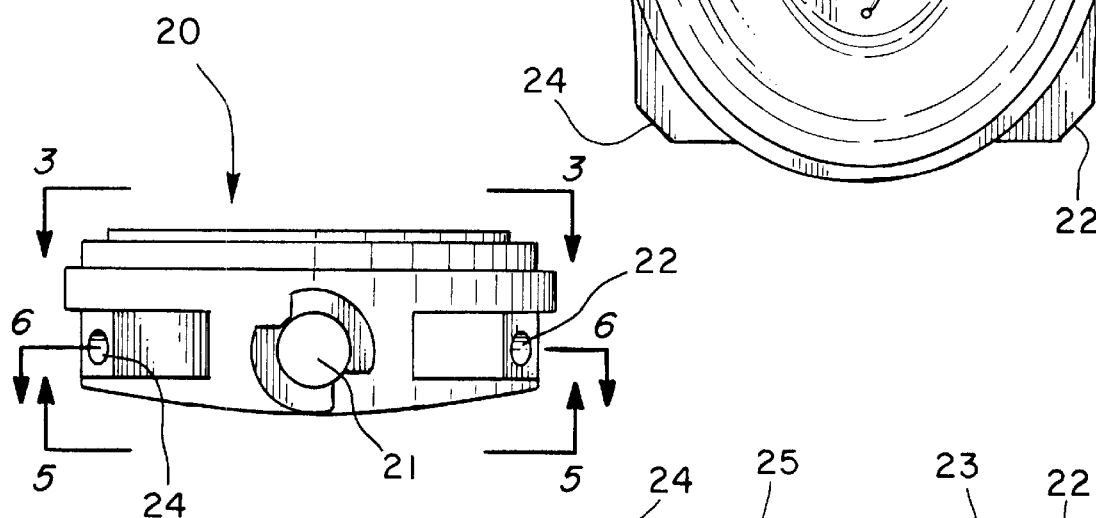
FIG. 4 is an end view of the housing of the device corresponding to FIG. 3.
Figure 5:
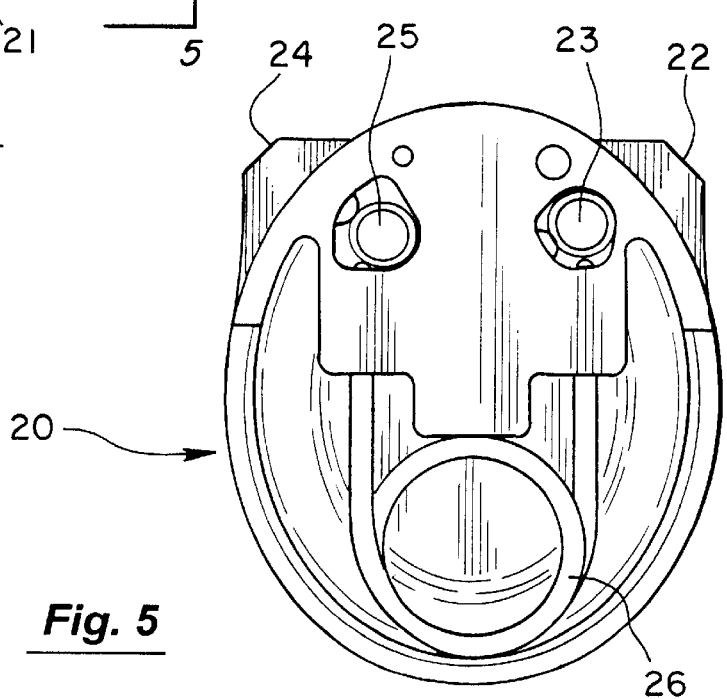
FIG. 5 is a bottom view of the housing of the device with the bottom cover removed.

The present device 20 has a housing with an inlet port 22 that can be connected to the tube 12 leading from the infusion pump 10, and outlet port 24 that can be connected to the tube 14 leading to the catheter 15. Both ports 22, 24 lead to a generally cylindrical valve opening 21 that extends inward from one edge of the device housing 20 as shown in FIG. 2. FIG. 3 is a top view of the device housing 20. FIG. 4 is an end view of the device housing 20 corresponding to FIG. 3. FIG. 5 is a bottom view of the device housing 20 with the bottom cover removed.

Figure 7:
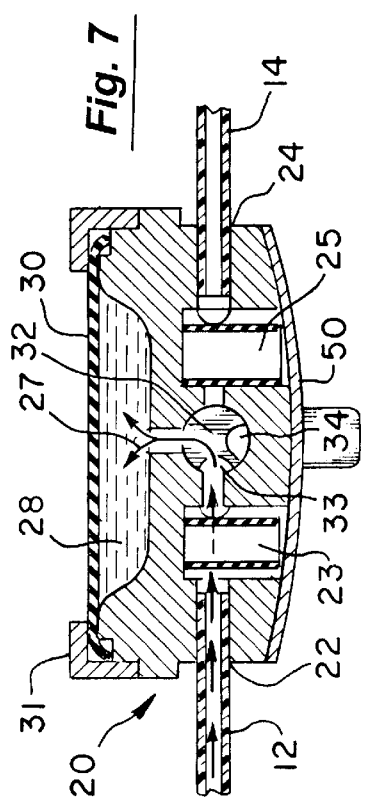
FIG. 7 is a vertical cross-sectional view of the device corresponding to FIG. 6.

A movable member 30 (e.g., a flexible diaphragm) is sealed about a region of the device housing 20 to define a fluid storage chamber 28 between the surface of the housing 20 and the movable member 30 as shown in FIG. 7. For example, a diaphragm 30 can be secured to the housing 20 by means of a retaining ring 31 that clips over a raised flange on the housing 20, as depicted in the exploded perspective view provided in FIG. 2. The fluid storage chamber 28 is connected to the cylindrical valve opening 21 by a small passageway 27 extending through the device housing 20 that permits fluid to flow into and out of the chamber 28 via the valve opening 21. In particular, the fluid storage chamber 28 can be compressed by manually exerting pressure on the movable member 30 by means of a thumb or finger. This causes fluid to flow from the chamber 28 through the passageway 27 and into the valve opening 21. Alternatively, the movable member 30 could be a piston, bellows, or movable button.

A rotatable valve member 32 is inserted into the valve opening 21. The valve member 32 has an external handle 35 that provides a finger-grip for turning the valve member 32 with respect to the device housing 20 and valve opening 21. The distal portion of the valve member 32 that is inserted into the valve opening 21 has a generally complementary shape (i.e., a cylindrical or tapered cylindrical shape) to maintain a fluid-tight seal. However, the surface of the valve member 32 also includes a first channel 33 (FIG. 6) that directs fluid from the inlet port 22 into the fluid storage chamber 28 when the valve member 32 is in a first rotational position with respect to the valve opening 21, and a second channel 34 (FIG. 8) that directs fluid from the chamber 28 to the outlet port 24 when the valve member 32 is in a second rotational position. Alternatively, the functions of both channels 33 and 34 could be accomplished by a single channel that rotates from alignment with the inlet port 22 in the first rotational position, to alignment with the outlet port 24 in the second rotational position.

In the preferred embodiment of the present invention, the passageway 27 leading to the fluid storage chamber 28 is located near the distal end of the valve opening 21. The valve member 32 does not extend all of the way to the distal end of the valve opening 21, thereby leaving an enclosed region between the distal end of the valve member and distal end of the valve opening 21. This is shown most clearly in FIGS. 6, 8, and 10. In this embodiment, fluid flows along one of the channels 33, 34, though the enclosed region at the distal end of the valve opening, and through the passageway 27 leading to the fluid storage chamber 28.

It should be noted that this two-position valve assembly provides significant safety advantages. When the valve member 32 is in the first rotational position (i.e., the "fill" position), fluid is only permitted to flow from the fluid source 10 into the fluid storage chamber 28. In particular, the valve assembly prevents backflow from the patient 50 into the device 20, and also blocks uncontrolled forward flow from the fluid pump 10 to the patient 50 through the device 20. When the valve member 32 is in the second rotational position (the "flush" position), fluid is only permitted to flow from the fluid storage chamber 28 through the catheter 15 into the patient 50. Here again, the valve assembly prevents backflow from the fluid storage chamber 28 to the fluid pump 10, and also blocks uncontrolled forward flow form the fluid pump 10 to the patient 50 through the device 20. This further helps to ensure that the entire quantity of fluid stored in the fluid storage chamber 28, and only that quantity of fluid is dispensed to the patient in "flush" mode. When the valve member 32 is moved to intermediate position between the "fill" and "flush" position, no fluid flow is allowed into or out of the fluid storage chamber 28, or through the valve assembly.

Figure 6:
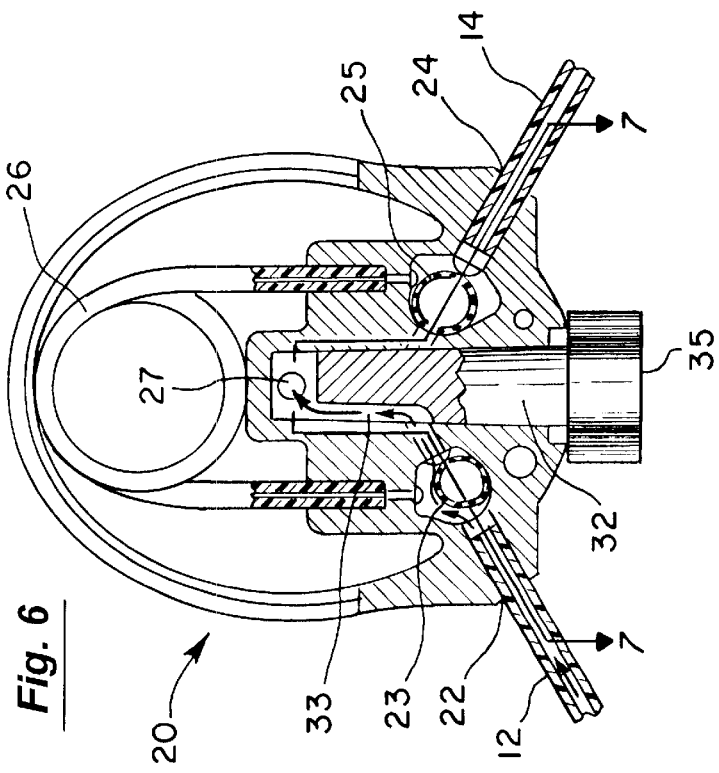
FIG. 6 is horizontal cross-sectional view of the device with the valve in a first position allowing fluid from the infusion pump to flow into the chamber beneath the diaphragm.
Figure 8:
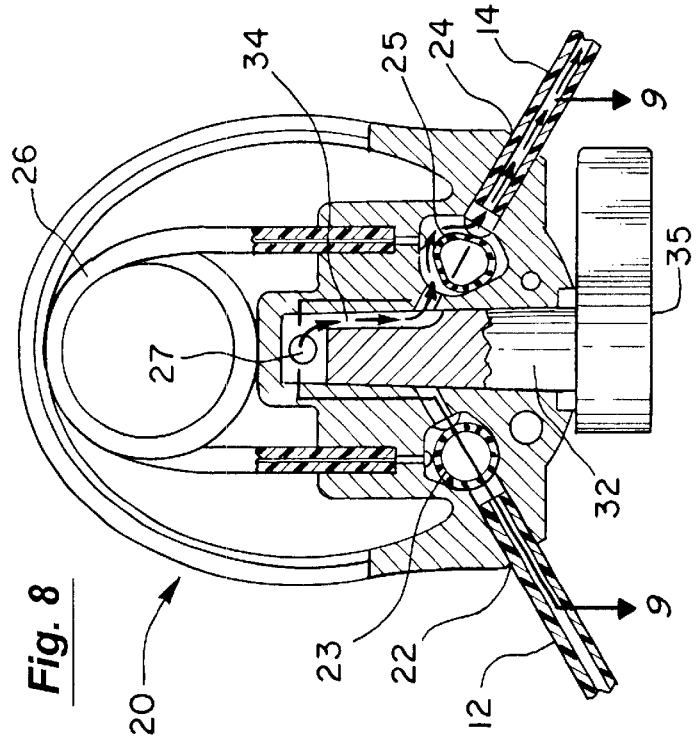
FIG. 8 is a horizontal cross-sectional view of the device with the valve in a second position allowing fluid from the chamber to be delivered to the catheter by exerting pressure on the diaphragm.

The present device can also be equipped with a KVO flow path 26 between the inlet and outlet ports 22, 24 to maintain a substantially constant, minimal flow (i.e., KVO flow) from the fluid source 10 to the catheter 15. As shown in FIGS. 6, 8, and 10, a loop of plastic tubing 26 having a very small diameter bore extends from the inlet port 22 to the outlet port 24 and completely bypasses the valve assembly 21, 32 regardless of the position of the valve member 32. The small bore of the KVO tubing 26 serves as a severe flow restriction that limits total flow along the KVO flow path to a fraction of a milliliter per hour.

The present device 20 can also be equipped with one-way valves 23, 25 and the inlet and outlet ports 22, 24, respectively, to prevent backflow, as shown in FIGS. 6, 8, and 10. In particular, the one-way valve 23 at the inlet port 22 allows flow from the fluid source 10 into the device 20, but prevents backflow from the catheter 15 or fluid storage chamber 28. Similarly, the one-way valve 25 at the outlet port 24 allows flow from the fluid storage chamber 28 to the catheter 15, but prevents backflow from the catheter 15 or the KVO flow path into the fluid storage chamber 28. A contoured bottom cover 40 attaches to the rear of the device housing 20 and encloses the KVO tubing 26 and one-way valves 23, 25 to maintain structural integrity of the device and prevent contamination.

The surface of the housing 20 beneath the diaphragm 30 includes a small bump 29 as illustrated in FIG. 2. As the user presses downward on the diaphragm 30 and collapses the fluid storage chamber 28, the bump 29 eventually comes into contact with the underside of the diaphragm and provides a tactile indication to the user's thumb or finger that the fluid storage chamber 28 is empty.

Operation

The following is a summary of various modes of operation of the present invention to flush a catheter 15 prior to administering a dose of medication. Prior to flushing the catheter 15, the fluid storage chamber 28 must first be filled from the fluid source 10. The handle 35 of the valve member 32 is rotated into a vertical position (i.e., the "fill" position). FIG. 6 is a horizontal cross-sectional view of the device 20 with the valve member 32 in a "fill" position allowing fluid from the infusion pump to fill the chamber 28 beneath the movable member 30. A corresponding vertical cross-sectional view of the device in the "fill" state is shown in FIG. 7. This aligns the first channel 33 in the valve member 32 with the inlet port 22 so that fluid flows from the fluid source 10 through the inlet port 22 and passageway 27 into the fluid storage chamber 28. The movable member 30 gradually lifts upward away from the device housing 20 as the chamber 28 fills with fluid.

Figure 9:
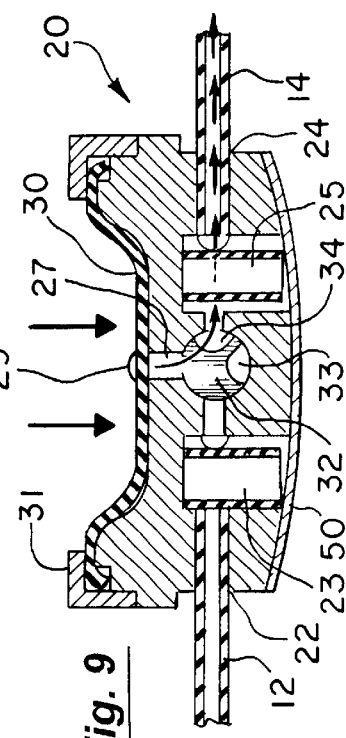
FIG. 9 is a vertical cross-sectional view of the device corresponding to FIG. 8.

After the chamber 28 has been filled, the user rotates the handle 35 to a second, horizontal position (i.e., the "flush" position). FIG. 8 is a horizontal cross-sectional view of the device 20 with the valve member 32 in the "flush" position allowing fluid from the chamber 28 to be delivered to the catheter 15 by exerting pressure on the movable member 30. A corresponding vertical cross-sectional view of the device in the "flush" state is shown in FIG. 9. In this position, the second channel 34 on the valve member 32 is rotated into alignment with the outlet port 24 so that fluid flows from the chamber 28 through the passageway 27 and outlet port 22 to the catheter 15. The movable member 30 is gradually depressed as fluid exits the chamber 28. Flow may continue until the chamber 28 has completely collapsed against the surface of the device housing 20 as depicted in FIG. 9. The raised bump 29 on the surface of the device housing 20 can be felt through the diaphragm 30 and signals the user that flushing is complete.

This processing of filling and flushing can be rapidly repeated as many times as necessary to deliver a series of surges of fluid through the catheter 15. The fluid storage chamber will automatically fill rapidly with fluid after the valve member 32 is rotated to the "fill" position. The valve member 32 can then easily rotated to the "flush" position. The flow rate exiting the fluid storage chamber 28 is controlled by the pressure exerted by the user on diaphragm 30. However, as a safety feature, it should be noted that uncontrolled forward flow cannot result, regardless of the position of the valve member 32.

FIGS. 10 and 11 are corresponding orthogonal cross-sectional views of the present device with the valve handle 35 in an intermediate position to allow only KVO flow. In the "KVO" state, neither of the channels 33 or 34 are aligned to allow flow through the device 20, or into or out of the fluid storage chamber 28. Hence, the only flow to the catheter 15 is the nominal KVO flow through the KVO tube 26. Alternatively, the device 20 can be kept with the valve handle 35 in the "flush" position to continue to provide a KVO flow, since the one-way valve 25 at the outlet port 24 prevents backflow from the catheter 15.

The present invention provides a completely enclosed fluid path from the fluid pump 10 to the patient 50. This helps to reduce the risk of infection, contamination, or other intravenous complications. In addition, the device 20 is separated from the injection site by a length of flexible tubing, which greatly reduces mechanical stress on the injection site and patient discomfort.

Other Fields of Use

It should be noted that the present invention can also serve a number of other uses. The device 20 can be employed to administer a bolus of medication as well as bolus basal medication. For example, the device 20 can be used as a means for administering a dose of analgesic medication on demand over time. The dosage is determined by the maximum volume of the fluid storage chamber 28. The present device can also be used to insert a medication spacer (e.g., saline solution or other patency fluid) between doses of incompatible medications.

The above disclosure sets forth a number of embodiments of the present invention. Other arrangements or embodiments, not precisely set forth, could be practiced under the teachings of the present invention and as set forth in the following claims.

I claim:

1. A catheter flushing device for connection between a fluid source and a patient's catheter, said catheter flushing device comprising:
   a housing having:
      (a) a valve opening;
      (b) an inlet port for connection with a fluid source;
      (c) an outlet port for connection with a patient's catheter; and
      (d) a KVO flow path through said housing between said inlet port and said outlet port maintaining substantially a constant, minimal flow from the fluid source to the catheter;
   a movable member sealed about a region of said housing and defining an enclosed chamber that can be compressed by exertion of pressure on said movable member;

said housing further having a passageway leading from said chamber to said valve opening; and a rotatable valve member within said valve opening having a channel directing fluid from said inlet port through said passageway and into said chamber in a first position, and a channel directing fluid from said chamber and said passageway to said outlet port in a second position when pressure is exerted on said movable member.

2. The catheter flushing device of claim 1 wherein said KVO flow path bypasses said valve opening and valve member.

3. The catheter flushing device of claim 1 wherein said KVO flow path further comprises a flow restrictor.

4. The catheter flushing device of claim 1 wherein said valve member does not allow flow, except when in said first and second positions.

5. The catheter flushing device of claim 1 wherein said valve opening and said valve member are substantially cylindrical.

6. The catheter flushing device of claim 1 further comprising a one-way valve at said inlet port preventing fluid flow from said chamber to the fluid source.

7. The catheter flushing device of claim 1 further comprising a one-way valve at said outlet port preventing fluid flow from the catheter into said chamber.

8. The catheter flushing device of claim 1 wherein said movable member comprises a flexible diaphragm.

9. A catheter flushing device for connection between a fluid source and a patient's catheter, said catheter flushing device comprising:

a housing having:
  (a) a valve opening
  (b) an inlet port for connection with a fluid source; and
  (c) an outlet port for connection with a patient's catheter;

a diaphragm sealed about a region of said housing and defining an enclosed chamber that can be compressed by exertion of pressure on said diaphragm;

said housing further having a passageway leading from said chamber to said valve opening;

a rotatable valve member within said valve opening having a channel directing fluid from said inlet port through said passageway and into said chamber in a first position, and a channel directing fluid from said chamber and said passageway to said outlet port in a second position when pressure is exerted on said diaphragm;

an inlet one-way valve at said inlet port preventing fluid flow from said chamber to the fluid source;

an outlet one-way valve at said outlet port preventing fluid flow from the catheter into said chamber; and a KVO flow path through said housing between said inlet port and said outlet port maintaining a minimal flow from said inlet port to said outlet port, and bypassing said valve opening and said valve member.

10. The catheter flushing device of claim 9 wherein said valve member does not allow flow, except when in said first and second positions.

11. The catheter flushing device of claim 9 wherein said valve opening and said valve member are substantially cylindrical.

12. The catheter flushing device of claim 9 wherein said KVO flow path further comprises a flow restrictor.

* * * * *